United States Patent [19]

Kawagishi et al.

[11] Patent Number: 4,659,652

[45] Date of Patent: Apr. 21, 1987

[54] SILVER HALIDE COLOR PHOTOGRAPHIC MATERIAL

[75] Inventors: Toshio Kawagishi; Kiyoshi Nakazyo, both of Kanagawa, Japan

[73] Assignee: Fuji Photo Film Co., Ltd., Kanagawa, Japan

[21] Appl. No.: 768,654

[22] Filed: Aug. 23, 1985

[30] Foreign Application Priority Data

Aug. 24, 1984 [JP]  Japan .................................. 59-176352

[51] Int. Cl.$^4$ ........................ G03C 1/08; G03C 7/00; G03C 7/26; G03C 7/32
[52] U.S. Cl. ..................................... 430/558; 430/548
[58] Field of Search ................................ 430/548, 558

[56]  References Cited

U.S. PATENT DOCUMENTS

| 4,524,132 | 6/1985 | Aoki et al. | 430/558 |
| 4,540,654 | 9/1985 | Sato et al. | 430/558 |
| 4,559,297 | 12/1985 | Seto et al. | 430/558 |

*Primary Examiner*—John E. Kittle
*Assistant Examiner*—Mukund J. Shah
*Attorney, Agent, or Firm*—Sughrue, Mion, Zinn, Macpeak & Seas

[57]  ABSTRACT

A silver halide color photographic material comprising a support having thereon at least one silver halide emulsion layer, wherein said material includes at least one magenta coupler of 1H-pyrazolo(1,5-b)(1,2,4)triazole type in which a substituted or unsubstituted aryloxy group is attached to the coupling active site to heighten coloring efficiency and speed, and further to ensure excellent light-fastness to the dye formed therefrom.

8 Claims, No Drawings

SILVER HALIDE COLOR PHOTOGRAPHIC MATERIAL

FIELD OF THE INVENTION

The present invention relates to a silver halide color photographic material, and particularly to a silver halide color photographic material having an improved color formability. More particularly, it is concerned with a silver halide color photographic material which contains a particular type of magenta coupler having a specific type of group at the coupling active site as a coupling eliminable group.

BACKGROUND OF THE INVENTION

In silver halide color photographic materials, the method of using light-sensitive silver halide emulsions and dye-forming couplers (also referred to simply as couplers hereinafter) which form dyes by reacting with oxidation products of aromatic primary amine developers is most frequently employed. As for the couplers, the combination of a yellow (dye-forming) coupler, a cyan coupler, and a magenta coupler is generally used.

Of such cuplers, 5-pyrazolone type couplers, which have frequently been employed as magenta couplers, still have serious problems to solve from the viewpoint of color reproduction. For example, azomethine dyes produced from the couplers of the above-described type have a side-absorption in the vicinity of 430 nm, exhibit a main absorption curve trailing a skirt of the long wavelength side, and so on.

With the intention of solving those problems, 1H-pyrazolo(1,5-b)(1,2,4)triazole type couplers have been developed as described in, for example, U.S. Patent Ser. No. 590,818 filed on Mar. 19, 1984. However, couplers of this type, although they solved the above-described problems of hue, have been found to have a problem in that the maximum color density of the developed image (written simply as Dmax hereinafter) is decreased because the rate of conversion from coupler into azomethine dye (referred to as "coloring efficiency" hereinafter) is low upon development-processing carried out under conditions that oxidation products of aromatic primary amine developers are generated in sufficient amounts in silver halide emulsion layers.

SUMMARY OF THE INVENTION

A first object of the present invention is to provide a silver halide color photographic material in which color-forming ability is enhanced by using a 1H-pyrazolo(1,5-b)(1,2,4)triazole type coupler which has undergone an improvement in coloring efficiency.

A second object of the present invention is to provide a novel silver halide photographic material in which the photographic speed is heightened by using a 1H-pyrazolo(1,5-b)(1,2,4)triazole type coupler having improved color-forming speed.

The above-described objects are attained with a silver halide color photographic material comprising a support having thereon at least one silver halide emulsion layer, wherein the material includes at least one 1H-pyrazolo(1,5-b)(1,2,4)triazole type magenta coupler in which a substituted or unsubstituted aryloxy group is bonded to the coupling active site.

DETAILED DESCRIPTION OF THE INVENTION

Magenta coupler of the foregoing type which can be advantageously employed include those represented by formula (I)

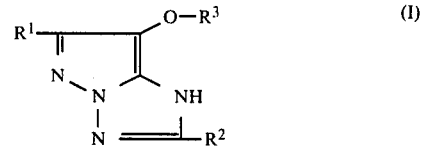

wherein $R^1$ and $R^2$ each represents a hydrogen atom or a certain substituent group and $R^3$ represents an aryl group, or $R^1$, $R^2$, or $R^3$ may be a linking group (including a simple bond) through which the coupler forms a polymer, including a dimer. The term "polymer" as used herein is intended to include compounds containing in a molecule two or more units derived from the coupler of formula (I); that is to say, from a bis compound to a polymeric coupler. The polymeric coupler may be a homopolymer constituted only with monomers containing the unit represented by formula (I) (and desirably, having an ethylenic unsaturated bond also, hereinafter a vinyl monomer), or a copolymer constituted not only of the foregoing coupler monomers, but also of non-coloring vinyl monomers which do not undergo coupling with oxidation products of aromatic primary amine developers.

In formula (I), $R^1$ and $R^2$ (which may be the same or different) each represents a hydrogen atom, a halogen atom, an aliphatic group, an aryl group, a heterocyclyl group, a cyano group, an alkoxy group, an aryloxy group, a heterocyclyloxy group, an acyloxy group, a carbamoyloxy group, a silyloxy group, a sulfonyloxy group, an acylamino group, an anilino group, a ureido group, an imido group, a sulfamoylamino group, a carbamoylamino group, an alkylthio group, an arylthio group, a heterocyclylthio group, an alkoxycarbonylamino group, an aryloxycarbonylamino group, a sulfonamido group, a carbamoyl group, an acyl group, a sulfamoyl group, a sulfonyl group, a sulfinyl group, an alkoxycarbonyl group, or an aryloxycarbonyl group.

$R^1$ or $R^2$ may represents a divalent group. In this case, the coupler of formula (I) can form a bis compound. When the unit represented by formula (I) is present in a vinyl monomer, $R^1$ or $R^2$ represents a mere linking group, and therethrough, the unit represented by formula (I) and a vinyl group combine.

More specifically, $R^1$ and $R^2$ each represents a hydrogen atom, a halogen atom (e.g., a chlorine atom, a bromine atom, etc.), an aliphatic group (including a straight or branched chain alkyl group containing from 1 to 32 carbon atoms, an aralkyl group, an alkenyl group, an alkynyl group, a cycloalkyl group and a cycloalkenyl group, which each may be substituted with a group of the kind which binds with its oxygen atom, nitrogen atom, a sulfur atom, or carbonyl group, a hydroxyl group, an amino group, a nitro group, a carboxy group, a cyano group, or a halogen atom, with specific examples including a methyl group, propyl group, t-butyl group, trifluoromethyl group, tridecyl group, 2-methanesulfonylethyl group, 3-(3-pentadecylphenoxy)-propyl group, 3-{4{2-[4-(4-hydroxyphenylsulfonyl)-phenoxy]dodecaneamido}phenyl}propyl group, 2- ethoxytridecyl group, cyclopentyl group, 3-(2,4-di-t-amylphenoxy)propyl group, and so on), an aryl group (e.g., a phenyl group, 4-t-butylphenyl group, 2,4-di-t-amylphenyl group, 4-tetradecaneamidophenyl group, etc.), a heterocyclyl group (e.g., a 2-furyl group, 2-thienyl group, 2-pyrimidinyl group, 2-benzothiazolyl group, etc.), a cyano group, an alkoxy group (e.g., a methoxy group, ethoxy group, 2-methoxyethoxy group, 2-dodecyloxyethoxy group, 2-methanesulfonylethoxy group, etc.), an aryloxy group (e.g., a phenoxy group, 2-methylphenoxy group, 4-t-butylphenoxy group, etc.), a heterocyclyloxy group, (e.g., a 2-benzimidazolyloxy, etc.), an acyloxy group (e.g., acetoxy group, hexadecanoyloxy group, etc.), a carbamoyloxy group (e.g., a N-phenylcarbamoyloxy group, N-ethylcarbamoyloxy, etc.), a silyloxy group (e.g., trimethylsilyloxy group, etc.), a sulfonyloxy group (e.g., dodecylsulfonyloxy group, etc.), an acylamino group (e.g., acetamido group, benzamido group, tetradecanamido group, α-(2,4-di-t-amylphenoxy)butylamido group, γ-(3-t-butyl-4-hydroxyphenoxy)butylamido group, α-{4-(4-hydroxyphenylsulfonyl)phenoxy}decanamido group, etc.), an anilino group (e.g., phenylamino group, 2-chloroanilino group, 2-chloro-5-tetradecanamidoanilino group, 2-chloro-5-dodecyloxycarbonylanilino group, N-acetylanilino group, 2-chloro-5-{α-(3-t-butyl-4-hydroxyphenoxy)-dodecanamido}anilino group, etc.), an ureido group (e.g., phenylureido group, methylureido group, N,N-dibutylureido group, etc.), an imido group (e.g., N-succinimido group, 3-benzylhydantoinyl group, 4-(2-ethylhexanoylamino)phthalimido group, etc.), a sulfamoylamino group (e.g., N,N-dipropylsulfamoylamino group, N-methyl-N-decylsulfamoylamino group, etc.), an alkylthio group (e.g., methylthio group, octylthio group, tetradecylthio group, 2-phenoxyethylthio group, 3-phenoxypropylthio group, 3-(4-t-butylphenoxy)propylthio group, etc.), an arylthio group (e.g., phenylthio group, 2-butoxy-5-t-octylphenylthio group, 3-pentadecylphenylthio group, 2-carboxyphenylthio group, 4-tetradecanamidophenylthio group, etc.), a heterocyclylthio group (e.g., 2-benzothiazolylthio group, etc.), an alkoxycarbonylamino group (e.g., methoxycarbonylamino group, tetradecyloxycarbonylamino group, etc.), an aryloxycarbonylamino group (e.g., phenoxycarbonylamino group, 2,4-di-tert-butylphenoxycarbonylamino group, etc.), a sulfonamido group (e.g., methanesulfonamido group, hexadecanesulfonamido group, benzenesulfonamido group, p-toluenesulfonamido group, octadecanesulfonamido group, 2-methyloxy-5-t-butylbenzenesulfonamido group, etc.), a carbamyl group (e.g., N-ethylcarbamoyl group, N,N-dibutylcarbamoyl group, N-(2-dodecyloxyethyl)carbamoyl group, N-methyl-N-dodecylcarbamoyl group, N-{3-(2,4-di-tert-amylphenoxy)propyl}carbamoyl group, etc.), an acyl group (e.g., acetyl group, (2,4-di-tert-amylphenoxy)acetyl group, benzoyl group, etc.), a sulfamoyl group (e.g., N-ethylsulfamoyl group, N,N-dipropylsulfamoyl group, N-(2-dodecyloxyethyl)sulfamoyl group, N-ethyl-N-dodecylsulfamoyl group, N,N-diethylsulfamoyl group, etc.), a sulfonyl group (e.g., methanesulfonyl group, octanesulfonyl group, benzenesulfonyl group, toluenesulfonyl group, etc.), a sulfinyl group (e.g., octanesulfinyl group, dodecylsulfinyl group, phenylsulfinyl group, etc.), an alkoxycarbonyl group (e.g., methoxycarbonyl group, butyloxycarbonyl group, dodecyloxycarbonyl group, octadecyloxycarbonyl group, etc.), or an aryloxycarbonyl group (e.g., phenoxycarbonyl group, 3-pentadecylphenoxycarbonyl group, etc.).

Specific examples of divalent group represented by $R^1$ or $R^2$ when the coupler forms a bis compound therethrough include a substituted or unsubstituted alkylene group (e.g., methylene group, ethylene group, 1,10-decylene group, —CH$_2$CH$_2$—O—CH$_2$CH$_2$—, etc.), a substituted or unsubstituted phenylene group (e.g., 1,4-phenylene group, 1,3-phenylene group,

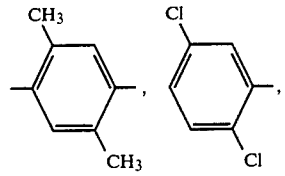

etc.), —NHCO—$R^5$—CONH— group (wherein $R^5$ represents a substituted or unsubstituted alkylene or phenylene group), and so on.

Specific examples of linking groups represented by $R^1$ or $R^2$ when the coupler of formula (I) is present in a vinyl monomer include combined groups formed by properly connecting groups selected from a class consisting of substituted or unsubstituted alkylene group (e.g., methylene group, ethylene group, 1,10-decylene group, —CH$_2$CH$_2$OCH$_2$CH$_2$—, etc.), substituted or unsubstituted phenylene groups (e.g., 1,4-phenylene group, 1,3-phenylene group,

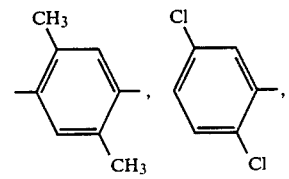

etc.), —NHCO—, —CONH—, —O—, —OCO—, and aralkylene groups (e.g.,

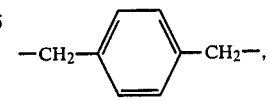

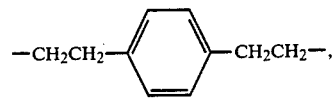

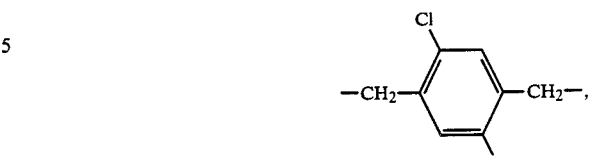

etc.).

Further, the vinyl group constituting the vinyl monomer may have another substituent group in addition to the coupler unit represented by formula (I). Suitable examples of such substituent groups include a halogen atom (e.g., a chlorine atom) and lower alkyl groups containing from 1 to 4 carbon atoms.

As suitable examples of non-coloring ethylenic monomers, which do not undergo the coupling reaction with oxidation products of aromatic primary amine developers, mention may be made of acrylic acid, α-chloroacrylic acid, α-aracrylic acid (e.g., methacrylic acid, etc.), esters or amides derived from these aryclic acids (e.g., acrylamide, n-butylacrylamide, t-butylacrylamide, diacetoneacrylamide, methacrylamide, methyl acrylate, ethyl acrylate, n-propyl acrylate, n-butyl acrylate, t-butyl acrylate, iso-butyl acrylate, 2-ethylhexyl acrylate, n-octyl acrylate, lauryl acrylate, methyl methacrylate, ethyl methacrylate, n-butyl methacrylate, and β-hydroxymethacrylate), methylenedibisacrylamide, vinyl esters (e.g., vinyl acetate, vinyl propionate and vinyl laurate), acrylonitrile, methacrylonitrile, aromatic vinyl compounds (e.g., styrene and derivatives thereof, vinyltoluene, divinylbenzene, vinylacetophenone, and sulfostyrene), itaconic acid, citraconic acid, crotonic acid, vinylidene chloride, vinyl alkyl ethers (e.g., vinyl ethyl ether), maleic acid, maleic anhydride, maleic acid esters, N-vinyl-2-pyrrolidone, N-vinylpyridine, 2- and 4-vinylpyridines, and so on. Two or more of these non-coloring ethylenic unsaturated monomers may be used in preparing the polymeric coupler of the present invention.

In formula (I), an aryl group represented by $R^3$ is a phenyl group or a naphthyl group, each of which may have one or more of substituent groups. Suitable examples of substituent groups which the phenyl or naphthyl group may have include halogen atoms (e.g., a fluorine atom, chlorine atom, bromine atom, etc.), alkyl groups (e.g., a methyl group, ethyl group, propyl group, t-butyl group, t-amyl group, t-octyl group, trifluoromethyl group, etc.), aryl groups (e.g., a phenyl group, etc.), heterocyclyl groups (e.g., a 2-furyl group, 2-thienyl group, 2-pyrimidinyl group, etc.), a cyano group, alkoxy group (e.g., a methoxy group, ethoxy group, 2-methoxyethoxy group, 2-dodecyloxyethoxy group, 2-methanesulfonylethoxy group, etc.), aryloxy groups (e.g., a phenoxy group, 2-methylphenoxy group, 4-t-butylphenoxy group, etc.), heterocyclyloxy groups (e.g., a 2-benzimidazolyloxy group, etc.), acyloxy groups (e.g., an acetoxy group, pivaloyloxy group, hexadecanoyloxy group, etc.), carbamoyloxy groups (e.g., a N-phenylcarbamoyloxy group, N-ethylcarbamoyloxy group, etc.), silyloxy groups (e.g., a trimethylsilyloxy group, etc.), sulfonyloxy groups (e.g., a dodecylsulfonyloxy group, etc.), acylamino groups (e.g., an acetamido group, benzamido group, tetradecanamido group, etc.), anilino groups (e.g., a phenylamino group, etc.), amino groups (e.g., a N,N-diethylamino group, etc.), ureido groups (e.g., a phenylureido group, etc.), imido groups (e.g., a N-succinimido group, etc.), sulfamoylamino groups (e.g., a N,N-dimethylsulfamoylamino group, etc.), alkylthio groups (e.g., a methylthio group, octylthio groups, etc.), arylthio groups (e.g., a phenylthio group, etc.), heterocyclylthio groups (e.g., a 2-benzothiazolylthio group, etc.), a alkoxycarbonylamino groups (e.g., a methoxycarbonylamino group, etc.), aryloxycarbonylamino groups (e.g., a phenoxycarbonylamino group, etc.), sulfonamido groups (e.g., a methanesulfonamido group, benzenesulfonylamido group, etc.), carbamoyl groups (e.g., a N,N-diethylcarbamoyl group, etc.), acyl groups (e.g., an acetyl group, benzoyl group, etc.), sulfamoyl groups (e.g., a N-ethylsulfamoyl group, N-ethyl-N-dodecylsulfamoyl group, etc.), sulfonyl groups (e.g., a butanesulfonyl group, toluenesulfonyl group, 4-hydroxyphenylsulfonyl group, etc.), sulfinyl groups (e.g., an octanesulfinyl group, benzenesulfinyl group, etc.), alkoxycarbonyl groups (e.g., a methoxycarbonyl group, octadecyloxycarbonyl group, etc.), aryloxycarbonyl groups (e.g., a phenoxycarbonyl group, 3-pentadecylphenoxycarbonyl group, etc.), a nitro group, a carboxyl group, and a sulfo group.

Specific examples of divalent groups represented by $R^3$ when two couplers units of formula (I) form a bis compound through $R^3$ include substituted or unsubstituted phenylene groups (e.g., 1,4-phenylene group, 1,3-phenylene group,

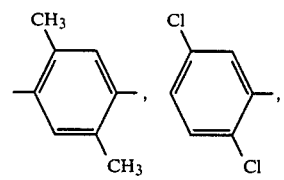

etc.), naphthylene group, a biphenylene group, and groups represented by formula (II)

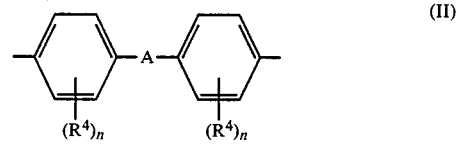

(II)

wherein A represents a divalent group, $R^4$ represents a certain substituent group, and n is an integer of 0 to 4, and more specifically, A represents a substituted or unsubstituted alkylene group, an oxygen atom, an amino group, a sulfur atom,

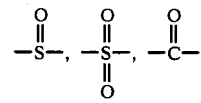

and so on, and $R^4$ represents an alkyl group (e.g., methyl, t-butyl, etc.), an alkoxy group (e.g., methoxy group, etc.), a hydroxyl group, a halogen atom (e.g., fluorine atom, chlorine atom, etc.), and so on.

Specific examples of typical magenta couplers to be employed in the present invention are illustrated below. However, the present invention should not be construed as being limited to the following examples. Ratios indicated are by weight, unless otherwise indicated.

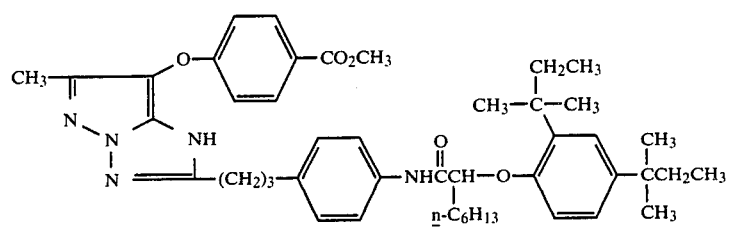 (M-1)
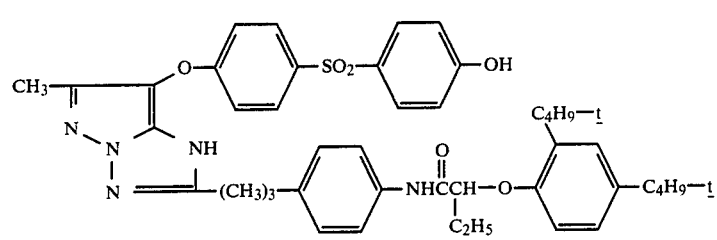 (M-2)
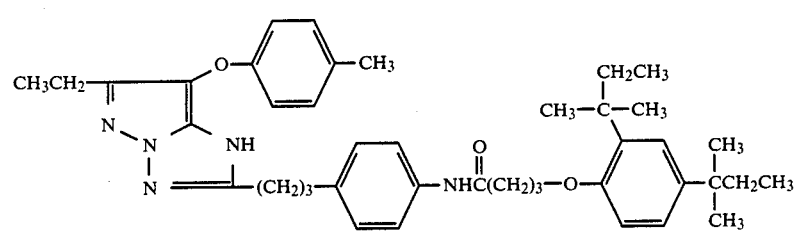 (M-3)
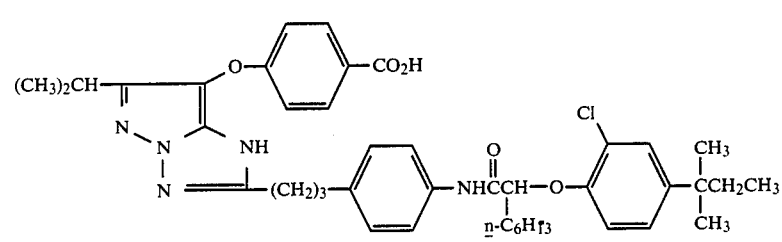 (M-4)
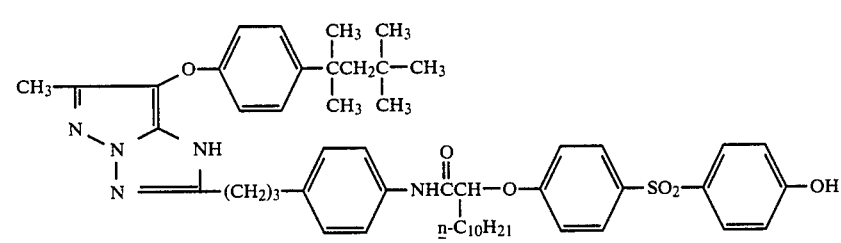 (M-5)
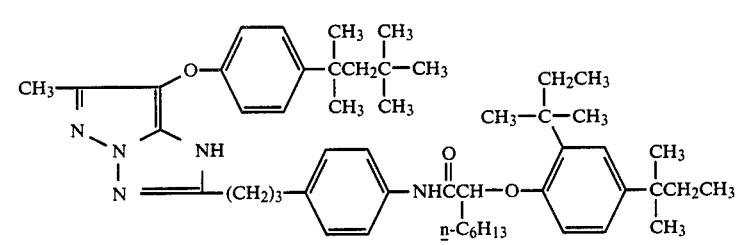 (M-6)

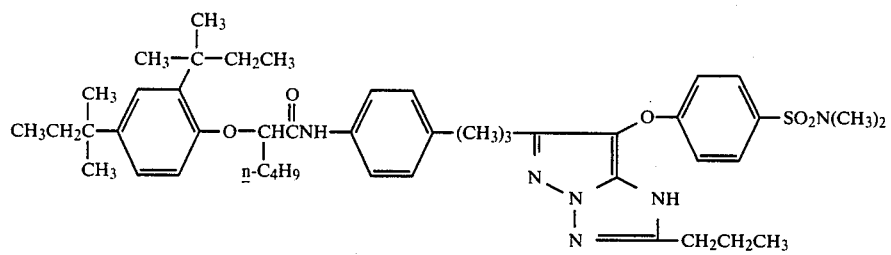
(M-7)
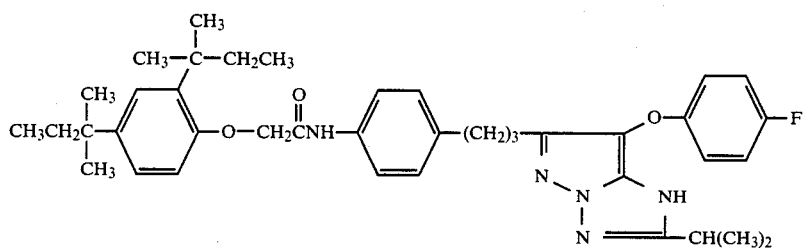
(M-8)
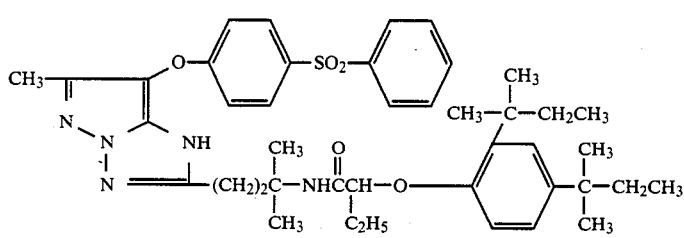
(M-9)
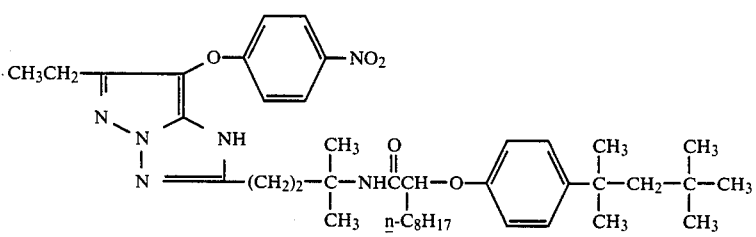
(M-10)
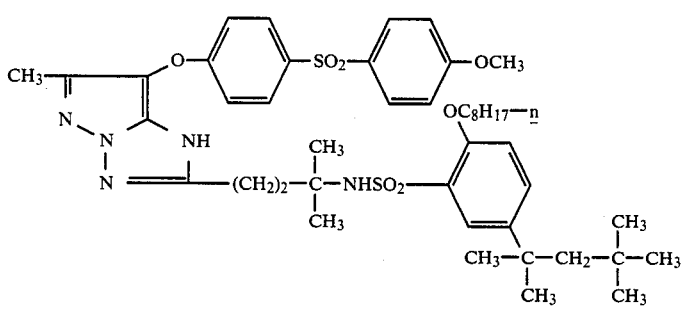
(M-11)
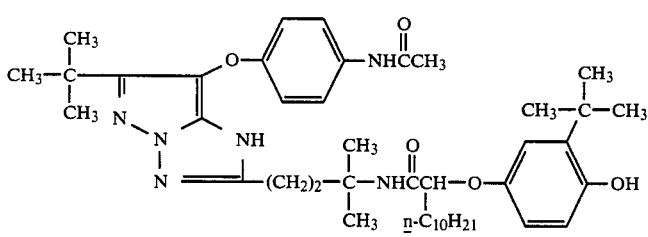
(M-12)

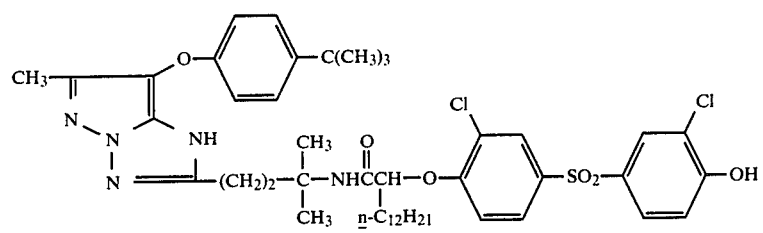
(M-13)
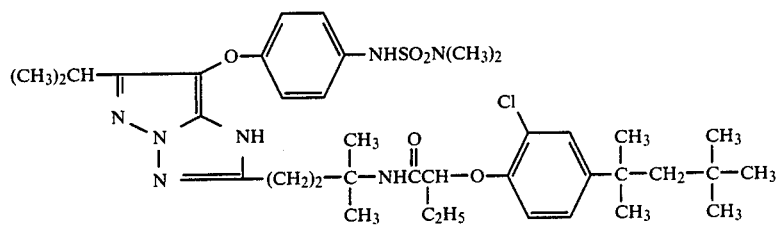
(M-14)
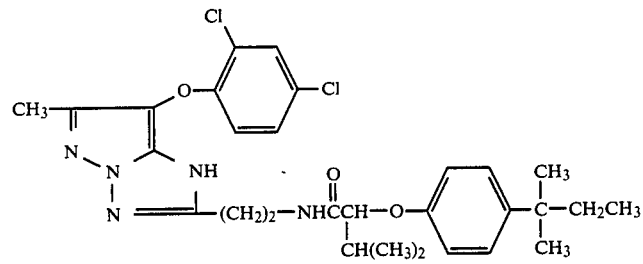
(M-15)
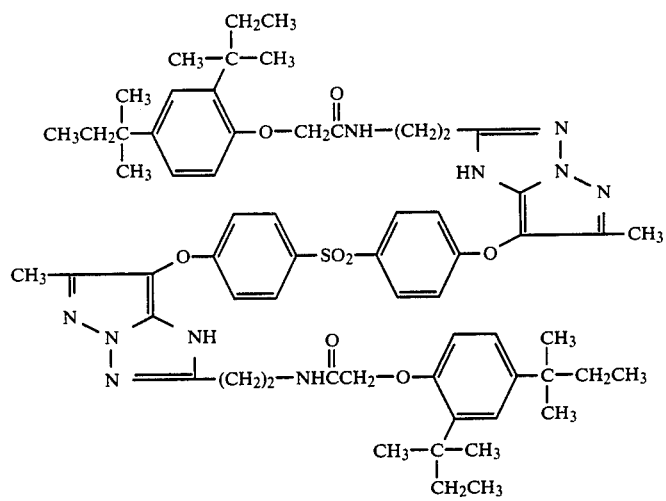
(M-16)
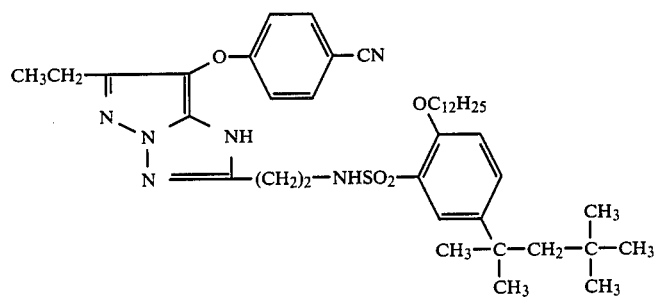
(M-17)

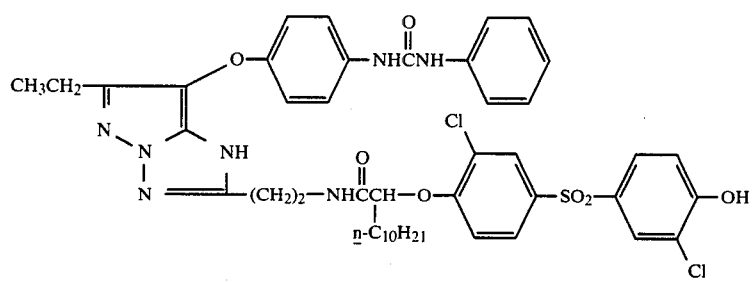
(M-18)
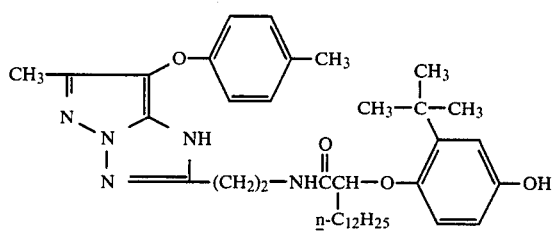
(M-19)
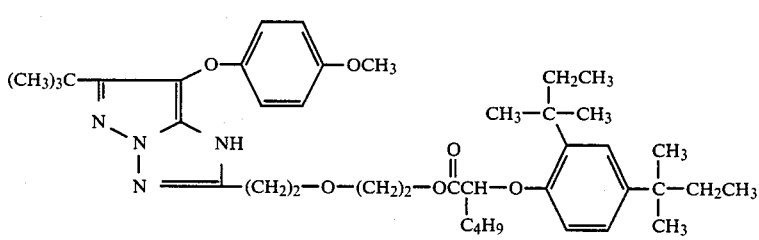
(M-20)
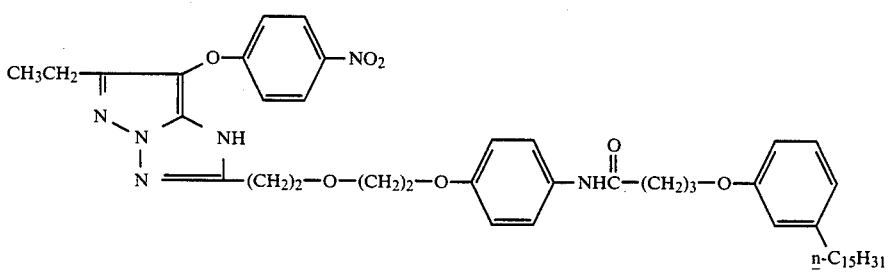
(M-21)
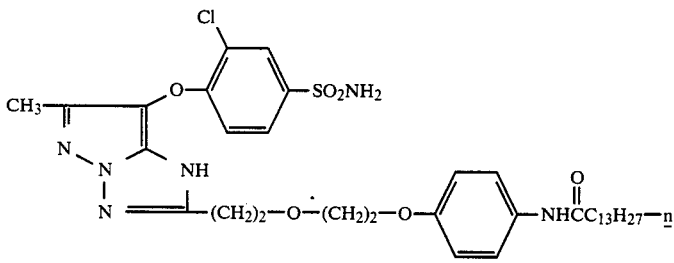
(M-22)
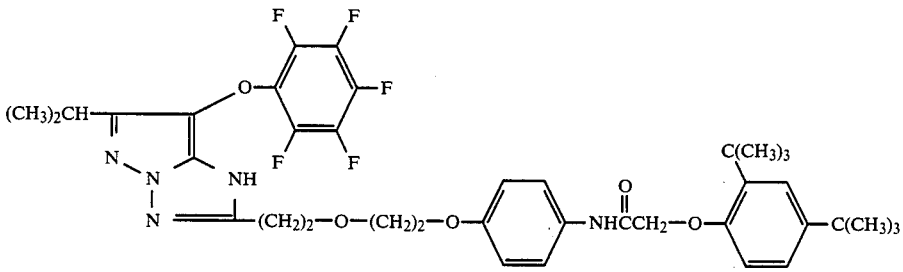
(M-23)

-continued
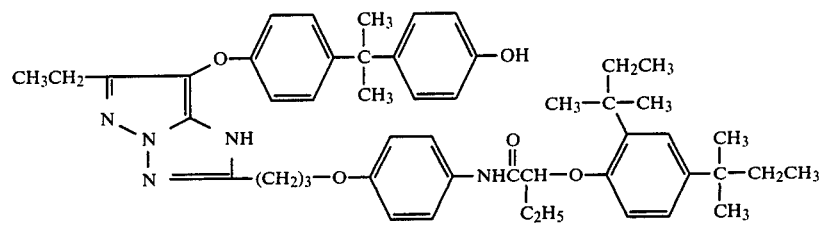
(M-24)
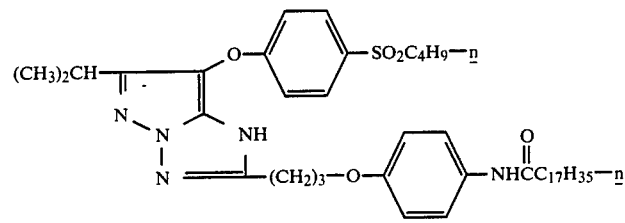
(M-25)
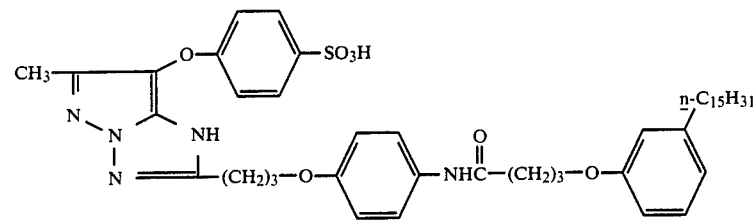
(M-26)
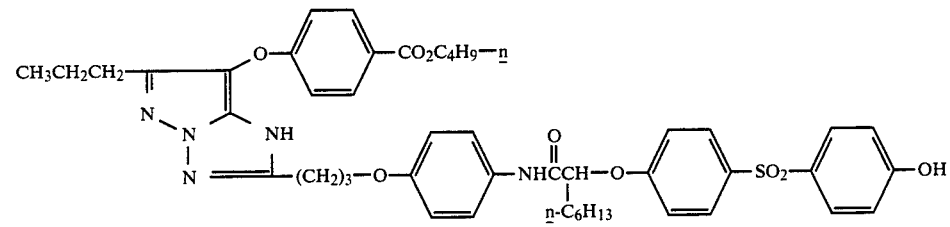
(M-27)
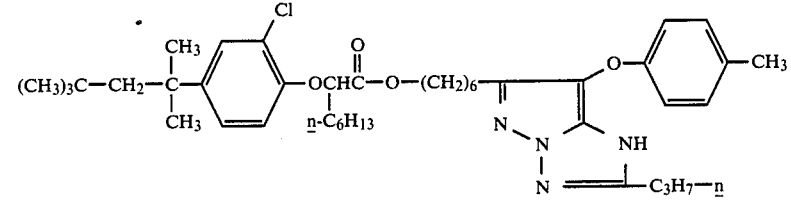
(M-28)
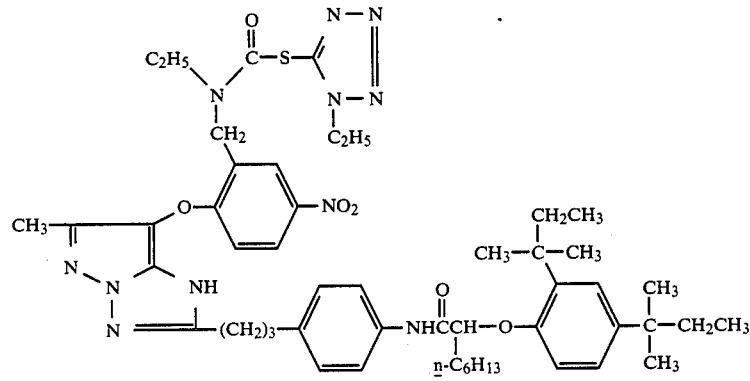
(M-29)

-continued
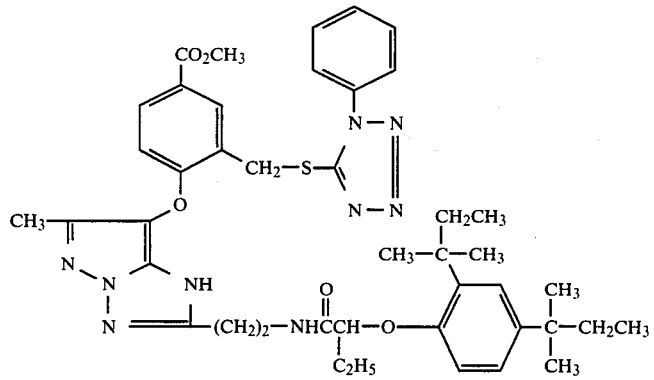 (M-30)
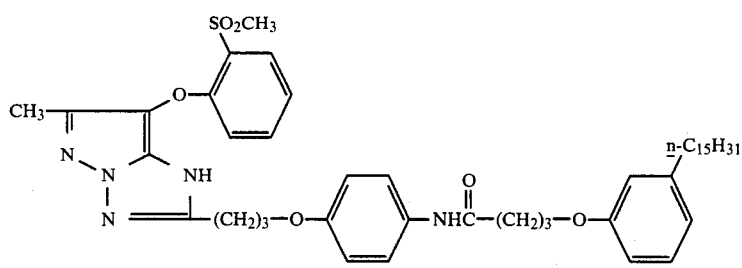 (M-31)
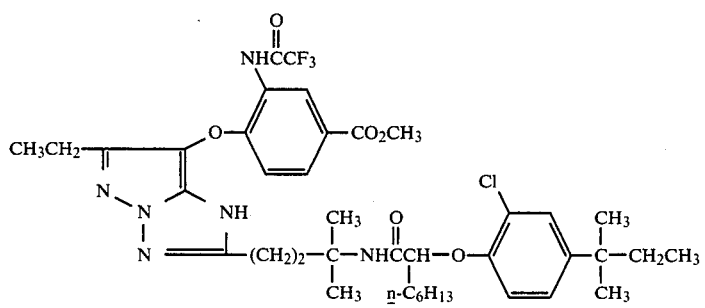 (M-32)
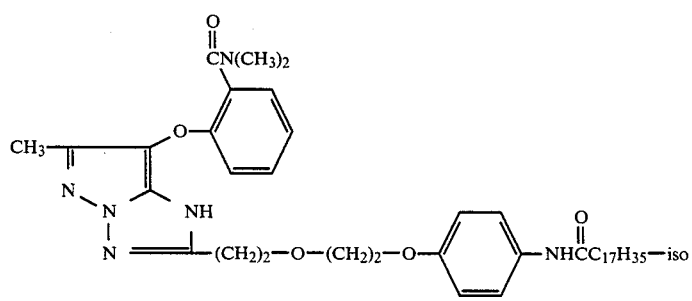 (M-33)
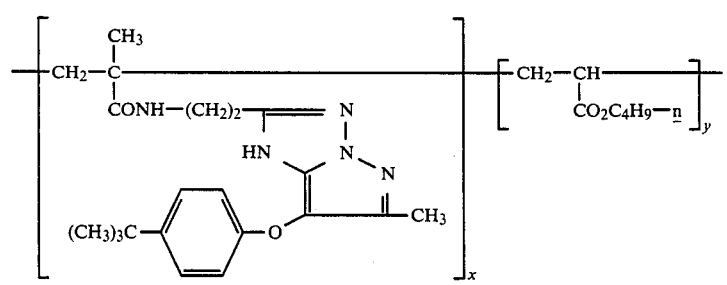 (M-34)
x/y = 50/50

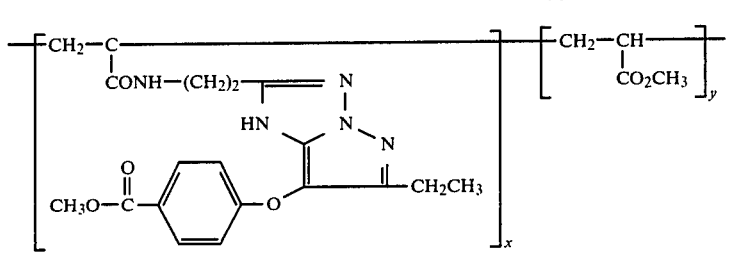
(M-35)
x/y = 45/55
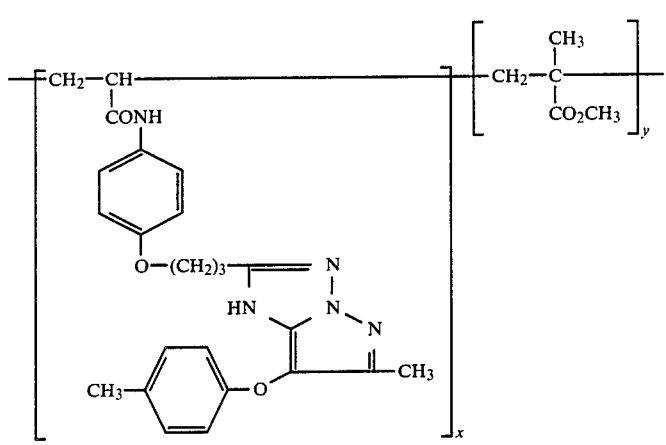
(M-36)
x/y = 45/55
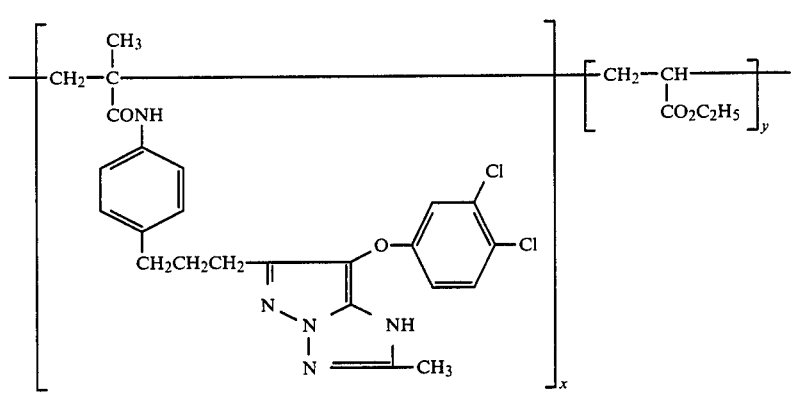
(M-37)
x/y = 50/50
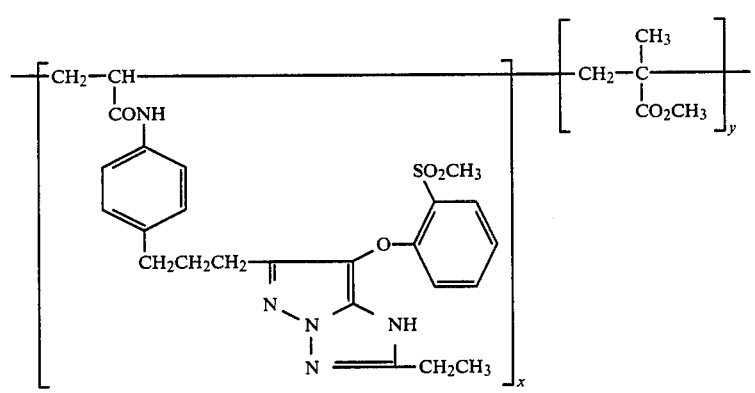
(M-38)
x/y = 45/55

-continued
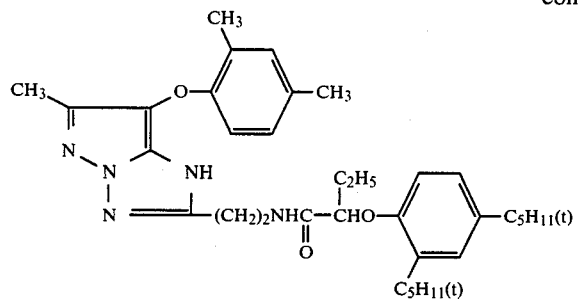
(M-39)
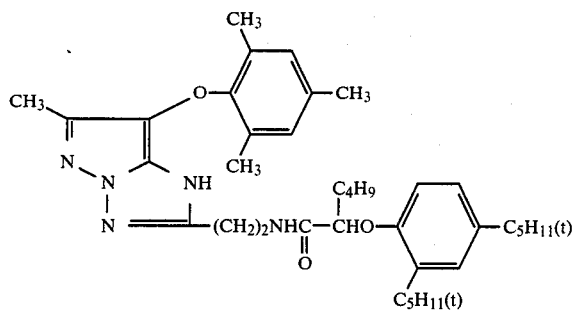
(M-40)
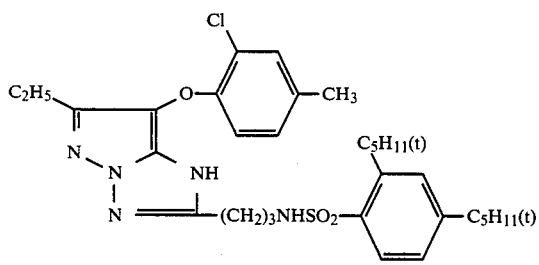
(M-41)
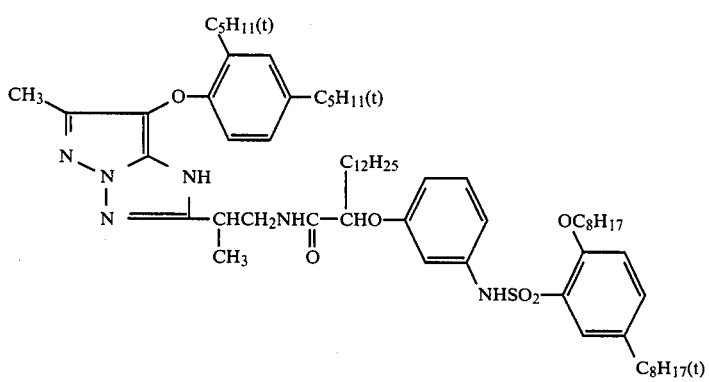
(M-42)
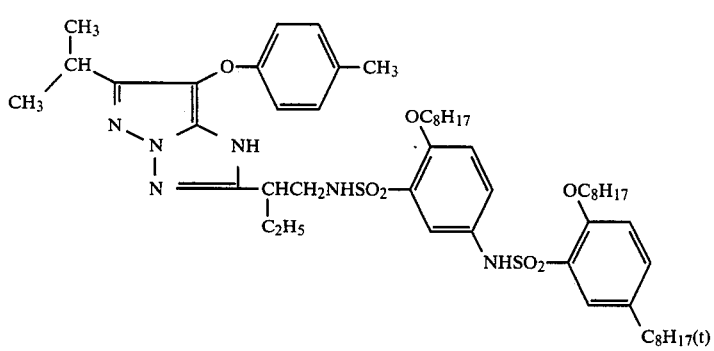
(M-43)
General methods for synthesizing the couplers to be used in the present invention are illustrated below.
The synthesis of the 1H-pyrazolo(1,5-b)(1,2,4)triazole skeleton of the couplers and connection of a ballast group thereto can be effected using the methods as described in Japanese Patent Application No. 27745/84 filed on Feb. 16, 1984 and U.S. Patent Ser. No. 714,989 filed on Mar. 20, 1985, and so on.

Methods for introducing an aryloxy group at the coupling active site are illustrated in detail below.

(1) One method comprises halogenating (e.g., chlorinating, brominating, or the like) the coupling active site, and then replacing the halogen atom by a phenoxy group, as illustrated by the following reaction scheme,

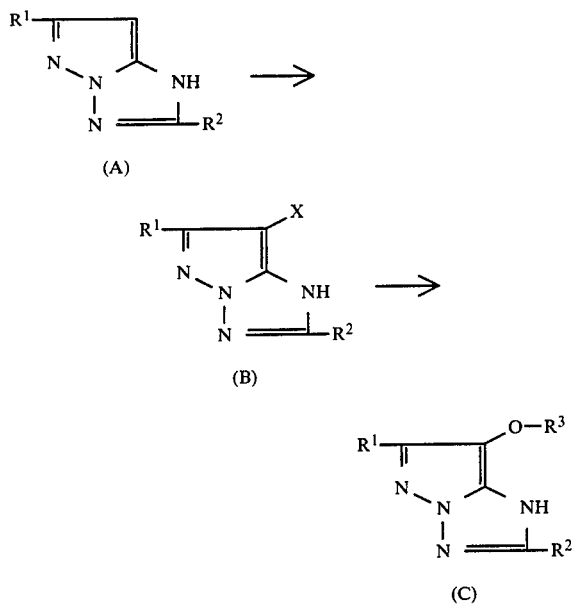

wherein X represents a halogen atom such as a bromine atom, a chlorine atom, etc.

More specifically, the halogenation at the coupling active site can be carried out with ease by acting one equivalent of a halogenating agent, such as bromine, N-bromosuccinimide, sulfuryl chloride, N-chlorosuccinimide or the like, on a four-equivalent coupler (A) in an inactive solvent like dichloromethane. Then, the halogenated body (B) is made to react with an appropriate $R^3$-OM, $(R^3$-O$)_2$M' or $(R^3$-O$)_3$M" (wherein $R^3$ represents an aryl group, and M, M' and M" represent a monovalent, a divalent, and trivalent metal ions, respectively) in an aprotic solvent, such as dimethylformamide (DMF), dimethyl sulfoxide (DMSO), hexamethylphosphoric triamide (HMPA), N-methyl-2-pyrrodidone or so on, resulting in formation of the desired compound (C) in which an aryloxy group is introduced at the coupling active site. More specifically, it is desired that the halogenated body (B) should be made to react with from the same to 20 times (molar basis) as much sodium or potassium phenolate as the halogenated body (B) at a temperature of 50° C. to 150° C. in from the same to 50 times (weight basis) as much the above-described solvent as the halogenated body (B). In addition, it happens that this reaction can be accelerated by the addition of a quaternary ammonium salt like tetrabutylammonium bromide or the like, or a halogenide of an alkali metal such as cesium bromide or the like.

(2) Another method comprises introducing an aryloxy group to the active methylene of a β-ketonitrile, and forming the 1H-pyrazolo(1,5-b)(1,2,4)triazole skeleton, as illustrated by the following reaction scheme,

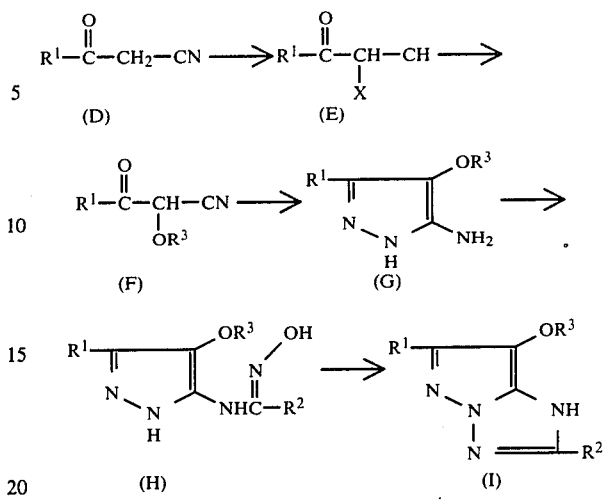

More specifically, a 3-oxonitrile (D) is treated with a halogenating agent, e.g., bromine, sulfuryl chloride, etc. in an inactive solvent such as dichloromethane or the like, to produce a halogenated body (E). The halogenated body is treated with a proper $R^3$-OH in the presence of a tertiary amine, or with a metal salt of formula $R^3$-OM as described above in the method (1), and thereby, it is converted to an aryloxy body (F). The thus obtained aryloxy body (F) is made to react with hydrazine hydrate in a proper solvent like ethanol to produce an aminopyrazole (G). From the aminopyrazole (G) can be prepared the desired coupler (I) to be used in the present invention according to the method described in Japanese Patent Application No. 70146/84 filed on Apr. 10, 1984. The 3-oxonitrile (D) can be synthesized using the methods as described in U.S. Pat. No. 4,411,753; German Patent Application (OLS) No. 3,209,472; Synthesis, p. 472 (1977); and so on.

In incorporating the couplers into silver halide emulsion layers in the present invention, known methods, e.g., the method described in U.S. Pat. No. 2,322,027, can be employed. Specifically, the couplers are dissolved in high boiling point solvents, such as phthalic acid alkyl esters (e.g., dibutyl phthalate, dioctyl phthalate, etc.), phosphoric acid esters (e.g., diphenyl phosphate, triphenyl phosphate, tricresyl phosphate, dioctylbutyl phosphate, etc.), citric acid esters (e.g., tributyl acetylcitrate), benzoic acid esters (e.g., octyl benzoate), alkylamides (e.g., diethyllauraylamide), fatty acid esters (e.g., dibutoxyethyl succinate, diethyl azelate, etc.), trimesic acid esters (e.g., tributyl trimesate) and so on, or in organic solvents having a boiling point ranging from about 30° C. to about 150° C., such as lower alkylacetates (e.g., ethyl acetate, butyl acetate, etc.), ethyl propionate, secondary butyl alcohol, methyl isobutyl ketone, β-ethoxyethylacetate, methyl cellosolve acetate, and so on, and then dispersed into hydrophilic colloids. The above-described high boiling solvents and low boiling point solvents may be used in the form of mixture of two or more thereof.

The magenta coupler to be employed in the present invention is preferably present in the silver halide emulsion layer in a range of 0.003 to 0.5 mole per mole of silver halide, more preferably 0.07 to 0.3 mole.

It is particularly desirable to use the couplers of the present invention together with phosphoric acid esters, especially those containing not less than 24 carbon atoms, because clearly colored dyes can be formed.

When they contain an acid group such as carboxylic acid, sulfonic acid or so on, the couplers can also be incorporated in hydrophilic colloids in the form of an alkaline aqueous solution.

As for the binder or the protective colloid of emulsion layers and interlayers to constitute the photographic material of the present invention, gelatin is used to advantage. Of course, other hydrophilic colloids can be also used alone or as combinations with gelatin.

In the preset invention, gelatin may be either lime-processed one or acid-processed one. Details of the preparation of gelatin are described in Arthur Veis, *The Macromolecular Chemistry of Gelatin,* Academic Press (1964).

Silver halide which may be used in photographic emulsion layers to constitute the photographic material of the present invention include silver bromide, silver iodobromide, silver iodochlorobromide, silver chlorobromide and silver chloride. Of these silver halide, silver iodobromide having an iodide content of 15 mole% or less is desirable. Especially good result can be obtained when silver iodobromide contains from 2 mole% to 12 mole% silver iodide.

The present invention is not particularly restricted as to mean grain size of silver halide grains in the photographic emulsion layer (The grain size herein refers to the grain diameter in case of grains spherical or approximately spherical in shape, while it refers to the edge length in the case of cubic grains. In both cases, it is represented by the mean based on the projected areas of grains.) However, it is preferably 3 microns or less. The distribution of the grain size can be either narrow or broad.

The silver halide grains in the photographic emulsions may have a regular crystal form, such as that of a cube, an octahedron or so on; an irregular crystal form, such as that of a sphere, a plate (tabular) or so on; or a composite form thereof. A mixture of various crystal forms of silver halide grains may be also present.

Photographic emulsions in which silver halide grains having a supertabular shape such that the grain diameter is not less than five times the grain thickness are contained in a fraction of 50% or more, based on the total projected area of all grains present therein, may be employed in the present invention.

A silver halide photographic emulsion which can be used in the present invention can be manufactured according to a method as disclosed in, for example, *Research Disclosure,* No. 17643 (December 1978), p. 22 to 23, "I Emulsion preparation and types" and No. 18716 (November 1979), p. 648.

Various photographic addenda which can be used in the present invention are disclosed, for example, in ibid, No. 17643, p. 23 to 28 and No. 18716, p. 648 to 651 as illustrated below.

| Examples of Addenda | RD No. 17643 Page | RD No. 18716 Page |
|---|---|---|
| (1) Chemical sensitizers | 23 | 648 right column |
| (2) Speed-increasing compound | | 648 right column |
| (3) Spectral sensitizers and supersensitizers | 23 to 24 | 648 right column to 649 right column |

-continued

| Examples of Addenda | RD No. 17643 Page | RD No. 18716 Page |
|---|---|---|
| (4) Antifoggants and stabilizers | 24 to 25 | 649 right column |
| (5) Light-absorbing material, filter dyes, scattering materials and ultraviolet absorbers | 25 to 26 | 649 right column to 650 left column |
| (6) Antistain agents | 25 right column | 650 left to right column |
| (7) Hardeners | 26 | 651 left column |
| (8) Vehicles and binding agents | 26 | 651 left column |
| (9) Plasticizers and lubricants | 27 | 650 right column |
| (10) Coating aids such as surfactants | 26 to 27 | 650 right column |
| (11) Agents for antistatic or conducting layers | 27 | 650 right column |

Suitable supports which can be used in the present invention are disclosed in, for example, ibid, No. 17643, p. 28 and No. 18716, p. 647 right column to 648 left column.

A color photographic light-sensitive material according to the present invention can be processed by a conventional method as disclosed, for example, in ibid, No. 17643, p. 28 to 29 and No. 18716, p. 651 from the left to the right column.

The present invention can also be applied to a multilayer multicolor photographic material having at least two different color sensitivities on a support. A multilayer color photographic material has, in general, at least one red-sensitive emulsion layer, at least one green-sensitive layer, and at least one blue-sensitive layer, on a support. The order of these layers can be varied as desired. Usually cyan-, magenta- and yellow-forming couplers are incorporated in red-, green-, and blue-sensitive emulsion layers, respectively. However, different combinations can be employed if desired.

In addition to the coupler represented by the foregoing formula (I), other dye forming couplers, that is to say, compounds capable of forming colors by coupling with the oxidation product of aromatic primary amine developing agent (e.g., phenylenediamine derivatives, aminophenol derivatives, etc.) upon color development processing, can be incorporated into the same or different photographic emulsion layers, or light-insensitive layers to constitute the photographic material of the present invention.

Typical examples of these color couplers include naphthol or phenol compounds, pyrazolone, or pyrazoloazole compounds, and open-chain or heterocyclic ketomethylene compounds. Specific examples of cyan, magenta and yellow couplers which can be used in the present invention are described in patent specifications cited in *Research Disclosure,* RD 17643, VII-D (December 1978) and RD 18717 (November 1979).

Of these couplers, non-diffusible couplers which contain a so-called ballast group in a molecule or have a polymerized form are more advantageous. Couplers having an eliminable group at the coupling active site are preferable to those having hydrogen atoms at such a site. In addition, couplers which can produce colored dyes having proper diffusibility, colored couplers, colorless couplers, or couplers capable of releasing development inhibitors or development accelerators upon development can also be used.

Representatives of yellow couplers which can be used in combination with the coupler of the present invention are oil protected type acylacetamide couplers. Specific examples thereof are described in U.S. Pat. Nos. 2,407,210, 2,875,057 and 3,265,506, and so on. Further, two-equivalent yellow couplers are preferred in the present invention. Typical examples of such two-equivalent couplers include oxygen atom-eliminable type yellow couplers as described in U.S. Pat. Nos. 3,408,194, 3,447,928, 3,933,501 and 4,401,752, and so on; and nitrogen atom-eliminable type yellow couplers as described in Japanese Patent Publication No. 10739/83, U.S. Pat Nos. 4,022,620 and 4,326,024, Research Disclosure, No. 18053 (April 1979), British Pat. No. 1,425,020, German Patent Application (OLS) Nos. 2,219,917, 2,261,361, 2,329,587, and 2,433,812, and so on. The characteristic of α-pivaloylacetoanilide type couplers is fastness of the dyes produced therefrom, while that of α-benzoylacetoanilide type couplers is excellent color developability.

As examples of magenta couplers which can be used in the present invention, mention may be made of oil protected type indazolone or cyanoacetyl couplers, preferably 5-pyrazolone couplers and pyrazoloazole couplers such as pyrazolotriazoles other than those of the present invention. Of couplers of the 5-pyrazolone type, those which are substituted with an arylamino group or an acylamino group at their 3-position are more desirable from the viewpoints of hue of colored dyes formed therefrom and color-forming speed. Typical examples of such couplers are described in U.S. Pat. Nos. 2,311,082, 2,343,703, 2,600,788, 2,908,573, 3,062,653, 3,152,896 and 3,936,015, and so on. Eliminable groups that may be present in two-equivalent 5-pyrazolone couplers are preferably nitrogen atom eliminable type ones as described in U.S. Pat. No. 4,310,619, or arylthio groups as described in U.S. Pat. No. 4,351,897. Further, 5-pyrazolone couplers having ballast groups as described in European Patent No. 73,636 are also desirable because of their high coloring reactivity.

As examples of pyrazoloazole couplers which can be used, mention may be made of pyrazolobenzimidazoles described in U.S. Pat. No. 3,369,897, preferably pyrazolo(5,1-c)(1,2,4)triazoles described in U.S. Pat. No. 3,725,067, pyrazolotetrazoles described in *Research Disclosure*, RD 24220 (June 1984), pyrazolopyrazoles described in Research Disclosure, RD 24230 (June 1984), and imidazopyrazoles described in Japanese Patent Application No. 45512/83.

Cyan couplers which can be used in the present invention include oil protected type naphthol and phenol couplers. As typical examples thereof, mention may be made of naphthol couplers as described in U.S. Pat. No. 2,474,293, more preferably oxygen atom eliminable type highly active two-equivalent naphthol couplers as described in U.S. pat. Nos. 4,052,212, 4,146,396, 4,228,233, and 4,296,200. Specific examples of phenol couplers which can be used are described in U.S. Pat. Nos. 2,396,929, 2,423,730, 2,772,162, 2,810,171 and 2,895,826, and so on.

Cyan couplers which are resistant to light, humidity, and high temperature are used to advantage in the present invention. Typical examples of such couplers include phenol type cyan couplers as described in U.S. Pat. No. 3,772,002; 2,5-diacylamino-substituted phenol type cyan couplers as described in U.S. Pat. Nos. 2,772,162, 3,758,308, 4,126,396, 4,334,011 and 4,327,173, German Patent Application (OLS) No. 3,329,729, Japanese Patent Application (OPI) No. 166956/84, and so on; and phenol type couplers which have a phenylureido group at their 2-position and further, an acylamino group at their 5-position, as described in U.S. Pat. Nos. 3,446,622, 4,333,999, 4,451,559, and 4,427,767.

With the intention of satisfying characteristics required of the photographic material, two or more of the above-described couplers can be incorporated into the same layer, and the same coupler can also be added to two or more different layers.

In order to compensate for undesired absorptions which colored dyes formed from conventional magenta and cyan couplers possess in a shorter wavelength region, it is desired that colored couplers should be used in proper combination in color sensitive materials for picture-taking. Typical examples of colored couplers are yellow-colored magenta couplers described in U.S. Pat. No. 4,163,670, Japanese Patent Publication No. 39413/82, and so on, and magenta-colored cyan couplers described in U.S. Pat. No. 4,004,929 and 4,138,258, British Pat. No. 1,146,368, and so on.

These color couplers which can be used together with the couplers of the present invention may form polymers including dimers. Typical representative polymeric couplers are described in U.S. Pat. Nos. 3,451,820 and 4,080,211. Specific examples of polymeric magenta couplers are described in British Pat. No. 2,102,173 and U.S. Pat. No. 4,367,282.

Further, the granularity can be improved by combined use with couplers of the type which form diffusible colored dyes. Specific examples of magenta couplers of such a type are described in U.S. Pat. No. 4,366,237 and British Pat. No. 2,125,570, and those of yellow, magenta, and cyan couplers of such a type are described in European Patent No. 96,873 and German Patent Application (OLS) No. 3,324,533.

The photographic material of the present invention can be laminated with a plastic film on both the surface and the back sides thereof after drying, subsequent to development-processing. Suitable examples of plastic films for lamination include polyolefins, polyesters, polyacrylates, polyvinyl acetate, polystyrene, butadiene-styrene copolymers, polycarbonates, and so on. Of these polymers, polyethylene terephthalate vinyl alcohol-ethylene copolymers and polyethylene are especially useful.

Synthesis examples of representative couplers of the present invention are illustrated in detail below.

SYNTHESIS EXAMPLE 1

Synthesis of Coupler (M-6):

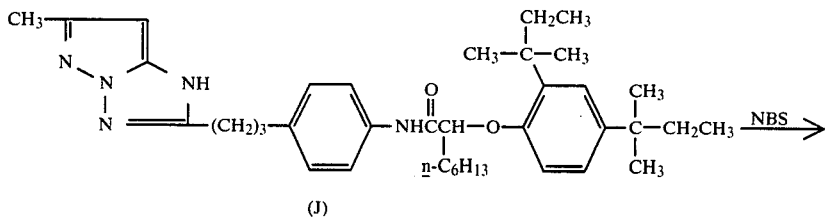

(J)

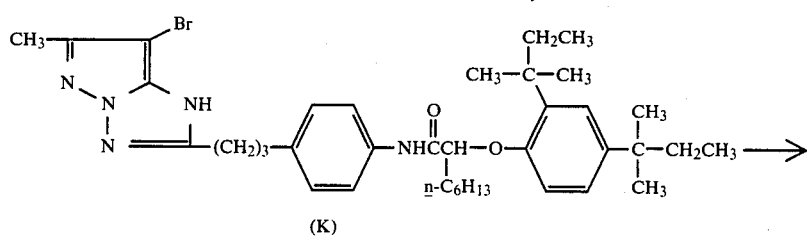

(K)

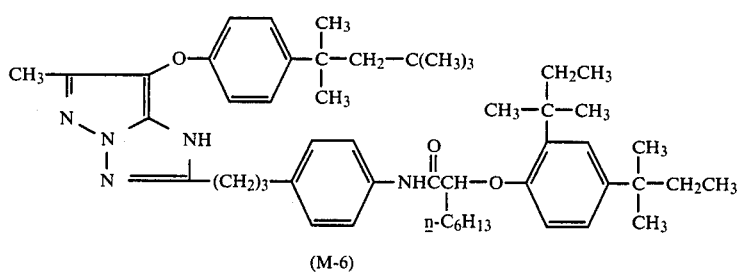

(M-6)

(1) Synthesis of Intermediate (K):

In a mixture of 100 ml of tetrahydrofuran and 500 ml of dichloromethane was dissolved 50.0 g of 6-methyl-2-(3-(4-(2-(2,4-di-tert-amylphenoxy)octaneamido)-phenyl)propyl)-1H-pyrazolo(1,5-b)(1,2,4)triazole (J). Thereto, 13.8 g of N-bromosuccinimide was added at room temperature, and stirring was continued for 30 minutes. The resulting reaction mixture was washed with 500 ml each of water for three times, and dried over anhydrous magnesium sulfate. An oily substance obtained by removing the solvent from the reaction mixture by distillation under reduced pressure was fractionated by chromatography on a column of silica gel (eluting solvent; hexane-ethyl acetate (3/1) mixture), and the eluate was concentrated and evaporated to dryness. Thus, the desired intermediate (K), 7-bromo-6-methyl-2-(3-(4-(2-(2,4-di-tert-amylphenoxy)octaneamido)phenyl)propyl)-1H-pyrazolo(1,5-b)(1,2,4)triazole, was obtained. Yield: 49.3 g (87%).

Nuclear Magnetic Resonance Spectrum (in CDCl$_3$):

δ(ppm): 12.46 (1H, s), 8.00 (1H, s), 7.33–6.65 (7H, m), 4.72 (1H, t), 2.83–2.50 (4H, m), 2.33 (3H, s), 2.1–1.2 (28H, m), 0.92–0.57 (9H, m).

(2) Synthesis of Coupler (M-6):

A 1.50 g portion of the above-described intermediate (K), 14.9 g of sodium 4-tert-octylphenoxide, and 14.0 g of tetrabutylammonium bromide were added to 75 ml of dimethyl sulfoxide. This mixture was stirred over a period of 8 hours as it was heated to 120° to 130° C. in a stream of nitrogen. After cooling, the resulting reaction mixture was dissolved in 300 ml of ethyl acetate, and washed with 300 ml each of 1N NaOH aqueous solution for six times and further, once with 300 ml of a saturated sodium chloride solution. The organic phase was dried over anhydrous magnesium sulfate, and then the solvent was removed therefrom by distillation under reduced pressure. The thus obtained oily substance was fractionated by chromatography on a column of silica gel (eluting solvent: hexane-ethyl acetate (3/1) mixture), and the eluate was concentrated and evaporated to dryness. Thus, the desired coupler (M-6) was obtained as a colorless powder. Yield: 8 g (45%).

Nuclear Magnetic Resonance Spectrum (in CDCl$_3$):

δ(ppm): 12.43 (1H, broad), 7.93 (1H, s), 7.30–6.59 (11H, m), 4.63 (1H, t), 2.9–2.4 (4H, m), 2.2–1.2 (39H, m), 0.9–0.5 (18H, m).

Mass Spectrometry (FD):

817 (M$^+$), 818 (M$^+$+1, b.p.).

| | Elemental Analysis | | |
|---|---|---|---|
| | C (%) | H (%) | N (%) |
| Calcd. | 76.33 | 9.24 | 8.56 |
| Found | 76.13 | 9.36 | 8.59 |

SYNTHESIS EXAMPLE 2

Synthesis of Coupler (M-1)

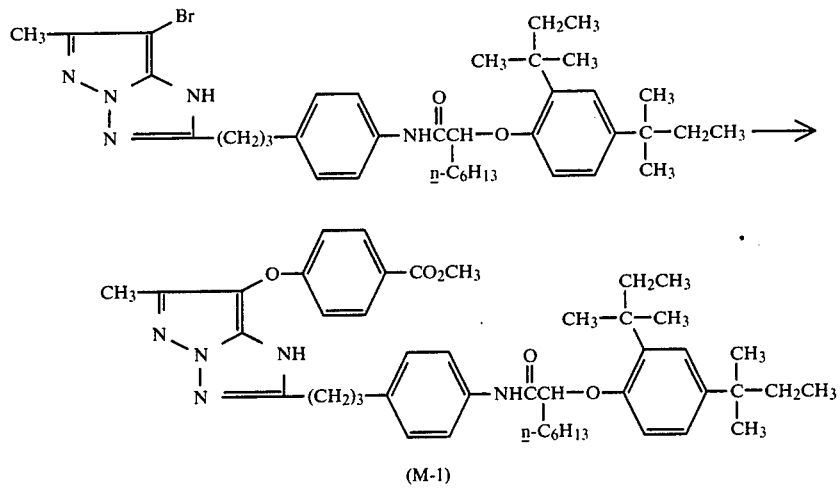

(M-1)

A 15.0 g portion of the foregoing intermediate (K) and 19.0 g of sodium 4-methoxycarbonylphenoxide were added to 75 ml of dimethyl sulfoxide. This mixture was stirred over a period of 8 hours as it was heated to 110° to 120° C. in a stream of nitrogen. After cooling, the resulting reaction mixture was dissolved in 400 ml of ethyl acetate, and washed with 600 ml each of 2N NaOH aqueous solution for three times and further, washed once with 500 ml of a saturated sodium chloride solution. The organic phase was dried over anhydrous magnesium sulfate, and the solvent was removed therefrom by distillation under reduced pressure. The thus obtained oily substance was fractionated by chromatography on a column of silica gel (eluting solvent: chloroform-ethyl acetate (10/1) mixture), and the eluate was concentrated and evaporated to dryness. Thus, the intended coupler (M-1) was obtained as a faintly yellow-colored powder. Yield: 4.3 g (26%).

Nuclear Magnetic Resonance Spectrum (in CDCl$_3$); δ (ppm): 12.17 (1H, s), 7.93 (1H, 3), 7.85 (2H, d, J=9 Hz), 7.32–6.98 (6H, m), 6.84 (2H, d, J=9 Hz), 6.63 (1H, d, J=9 Hz), 4.62 (1H, t), 3.79 (3H, s), 2.9–2.5 (4H, m), 2.4–1.1 (31H, m), 0.9–0.5 (9H, m).

Mass Spectrometry (FD): 764 (M$^+$+1, b.p.).

| | Elemental Analysis | | |
|---|---|---|---|
| | C (%) | H (%) | N (%) |
| Calcd. | 72.32 | 8.05 | 9.17 |
| Found | 72.21 | 8.05 | 9.08 |

The present invention is illustrated in greater detail by reference to the following examples. However, the present invention should not be construed as being limited to the following examples.

EXAMPLE 1

To 10 g of the magenta coupler (M-6) were added 20 ml of tri(2-ethylhexyl) phosphate and 25 ml of ethyl acetate. This mixture was converted into a solution by heating, and added to 100 ml of a water solution containing 10 g of gelatin and 1.0 g of sodium dodecylbenzenesulfonate. The mixed solutions were stirred at a high speed to be finely emulsified and dispersed. The total portion of the resulting emulsified dispersion was added to 100 g of a silver chlorobromide emulsion whose halide composition was 50 mol% bromide (in which 6.5 g of Ag was contained) and thereto, 10 ml of a 2% solution of sodium 2,4-dihydroxy-6-chloro-s-triazine was further added as hardener. The thus prepared composition was coated at a coverage of 200 mg silver per square meter on a paper support, both sides of which were laminated with polyethylene. On the layer coated was provided a gelatin layer to make a sample. This was designated as Sample A.

In addition, Samples B, C and D were produced in the similar manner as Sample A, except that 9.4 g of the coupler (M-1), 8.3 g of the coupler (M-9) and 7.9 g of the coupler (M-15) were employed in place of the coupler (M-6) as magenta coupler, respectively, and thereto were added 19 ml, 17 ml, and 16 ml of tri(2-ethylhexyl) phosphate instead of 20 ml thereof, respectively.

Further, a sample for comparison was produced in the similar manner as the above-described samples, except that 8.9 g of the compound illustrated below was employed in place of the magenta coupler of the present invention, and the addition amount of tri(2-ethylhexyl) phosphate was changed to 18 ml.

(Comparative compound)

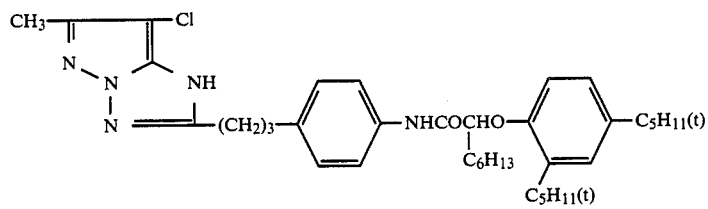

Each of Samples A to D, and the above-described comparative sample were subjected to wedgewise exposure of 1,000 C.M.S., and processed with the following processing solutions.

| Developing Solution: | |
|---|---|
| Benzyl Alcohol | 15 ml |
| Diethylenetriaminepentaacetic Acid | 5 g |
| KBr | 0.4 g |
| $Na_2SO_3$ | 5 g |
| $Na_2CO_3$ | 30 g |
| Hydroxylamine Sulfate | 2 g |
| 4-Amino-3-methyl-N—β-(methanesulfonamido)ethylaniline.3/2 $H_2SO_4.H_2O$ | 4.5 g |
| Water to make | 1,000 ml |
| pH | 10.1 |

| Bleach-fix Bath: | |
|---|---|
| Ammonium Thiosulfate | 150 ml |
| $Na_2SO_3$ | 5 g |
| Na[Fe(EDTA)] | 40 g |
| EDTA | 4 g |
| Water to make | 1,000 ml |
| pH | 6.8 |

Processing Step:

| | Temperature | Time |
|---|---|---|
| Development | 33° C. | 3 min. 30 sec. |
| Bleach-fix | 33° C. | 1 min. 30 sec. |
| Washing | 28–35° C. | 3 min. |

The thus processed samples each produced clear magenta dye images of high saturation. Photographic characteristics of these dye images were examined, and the results set forth below was obtained.

TABLE 1

| Sample | Sensitivity* (S) | Gradation (γ) | Maximum Density (Dm) |
|---|---|---|---|
| Comparison | 100 | 2.92 | 2.94 |
| A | 66 | 3.20 | 3.16 |
| B | 71 | 3.14 | 3.11 |
| C | 73 | 3.12 | 3.13 |
| D | 68 | 3.23 | 3.19 |

In Table 1, "*" was determined based on the exposure required for attaining a density of fog +0.5. It is shown as relative value, with the comparative sample being taken as 100.

As a result, it has turned out that the aryloxy group eliminable type couplers of the present invention were superior to halogen atom eliminable type couplers in sensitivity, gradation and maximum density. This is because the coupling activity was enhanced by introduction of an aryloxy group as coupling eliminable group and that, the coloring efficiency was heightened.

EXAMPLE 2

On a paper support both sides of which were laminated with polyethylene, were coated from the first layer (lowest layer) to the 7th layer (topmost layer), as described in Table 2, whereby color photographic materials E, F, and G were prepared.

Therein, the coating compositions containing the emulsified dispersions of the magenta couplers and the emulsions, which were used for forming the 3rd layer, were prepared according to the process of Example 1.

TABLE 2

| Support | Paper support laminated with polyethylene on both sides thereof |
|---|---|
| 1st Layer | Blue-sensitive silver chlorobromide emulsion (Br: 80 mol %, silver coverage: 350 mg/m$^2$), Gelatin (coverage: 1500 mg/m$^2$), Yellow coupler (*1) (coverage: 500 mg/m$^2$), Solvent (*2) (coverage: 400 mg/m$^2$) |
| 2nd Layer | Gelatin (coverage: 1100 mg/m$^2$), Color mixing inhibitor (*3) (coverage: 200 mg/m$^2$), Solvent (*4) (coverage: 100 mg/m$^2$) |
| 3rd Layer | Green-sensitive silver chlorobromide emulsion (Br: 50 mol %, Silver coverage: 180 mg/m$^2$), Magenta coupler (*5) (coverage: 3.4 × 10$^{-4}$ mol/m$^2$), Solvent (*6) (coverage: Sample E 510 mg/m$^2$, Sample F 480 mg/m$^2$, Sample G 410 mg/m$^2$) |
| 4th Layer | Gelatin (coverage: 1600 mg/m$^2$), Ultraviolet absorbing agent (*7) (coverage: 700 mg/m$^2$), Color mixing inhibitor (*3) (coverage: 200 mg/m$^2$), Solvent (*4) (coverage: 300 mg/m$^2$) |
| 5th Layer | Red-sensitive silver chlorobromide emulsion (Br: 50 mol %, silver coverage: 300 mg/m$^2$), Gelatin (coverage: 1200 mg/m$^2$), Cyan coupler (*8) (coverage: 400 mg/m$^2$), Solvent (*4) (coverage: 250 mg/m$^2$) |
| 6th Layer | Gelatin (coverage: 1000 mg/m$^2$), Ultraviolet absorbing agent (*7) (coverage: 360 mg/m$^2$), Solvent (*4) (coverage: 120 mg/m$^2$) |
| 7th Layer | Gelatin (coverage: 1600 mg/m$^2$) |

*1 Yellow coupler α-pivaloyl-α-(2,4-dioxo-5,5'-dimethyloxazolidine-3-yl)-2-chloro-5-[α-(2,4-di-tert-pentylphenoxy)butaneamido]aceto-anilide.
*2 Solvent Dioctyl butyl phosphate.
*3 Color mixing inhibitor 2,5-Dioctylhydroquinone.
*4 Solvent Dibutyl phthalate.
*5 Magenta coupler Sample E M-6, Sample F M-1, Sample G comparative compound used in Example 1.
*6 Solvent Tri(2-ethylhexyl) phosphate.
*7 Ultraviolet absorbing agent 2-(2-hydroxy-3-sec-butyl-5-tert-butyl-phenyl)benzotriazole
*8 Cyan coupler 2-[α-(2,4-di-tert-pentylphenoxy)butaneamino]-4,6-dichloro-5-methylphenol.

Each of these samples, E, F and G, was submitted to wedgewise exposure of 1,000 C.M.S. through a B-G-R (Blue-Green-Red) separation filter, and processed in the same manner as in Example 1, except that different color development times, 2 minutes, 3 minutes and 30 seconds, and 6 minutes, were selected.

Changes of photographic characteristics by change of color development time are summarized in Table 3.

TABLE 3

| Sample | Sensitivity (S)* | | | Gradation (γ) | | | Maximum Density (Dm) | | |
|---|---|---|---|---|---|---|---|---|---|
| | 2 min | 3.5 min | 6 min | 2 min | 3.5 min | 6 min | 2 min | 3.5 min | 6 min |
| E (M-6) | 81 | 67 | 63 | 3.15 | 3.16 | 3.12 | 2.85 | 2.85 | 2.84 |
| F (M-1) | 88 | 73 | 68 | 3.09 | 3.13 | 3.10 | 2.80 | 2.82 | 2.82 |
| G Comparative Compound | 126 | 100 | 83 | 2.62 | 2.81 | 2.79 | 2.50 | 2.63 | 2.64 |

In Table 2, "*" is relative values of exposures required for achieving the density of fog+0.5, with the comparative sample, which had received 3.5 minutes' development, being taken as 100.

These results demonstrate that in the multilayered samples of color photography also, the aryloxy group eliminable type couplers of the present invention were excellent couplers since they had small dependences of all of photographic characteristics, sensitivity, gradation and maximum density, upon color development time, compared with the halogen atom eliminable type coupler, and caused little changes in photographic characteristics for a short period of development time. Such high coupling activities and high coloring efficiencies demonstrated by the couplers of the present invention ensure greater advantages in designing products, compared with conventional pyrazoloazole type couplers.

EXAMPLE 3

The same samples E, F and G, as prepared in Example 2 were optionally exposed through a B-G-R separation filter and subjected to photographic processings in the same manners, respectively, as in Example 1 to produce color images.

A part of each sample processed was allowed to stand for 7 days at a high temperature of 100° C., another part thereof was allowed to stand for 6 weeks under high temperature and humidity conditions of 60° C. and 90% RH, and still another part thereof was exposed to light of a fluorescent lamp fitted in a Fade-o-meter (15,000 lux) for 4 weeks and thereby, fastness of the magenta dye images obtained was examined. The results obtained are shown in Table 4.

TABLE 4
(Fastness of Dye Image)

| Sample | Change of Magenta Dye Image in Density | | |
|---|---|---|---|
| | 100° C., 7 days | 60° C., 90% RH 6 weeks | Fluorescent lamp, 4 weeks |
| E (M-6) | 0.99 (0.15) | 0.98 (0.14) | 0.65 (0.13) |
| F (M-1) | 0.99 (0.14) | 0.97 (0.14) | 0.63 (0.13) |
| G (Comparative Compound) | 0.98 (0.16) | 0.97 (0.15) | 0.60 (0.14) |

In the above table, the values are densities of the magenta dye images after discoloration test, with their own initial values being taken as 1.0. The values in parentheses are densities (stain) measured through a blue filter in non-colored areas.

As can be seen from the results in Table 4, the color images produced from the couplers of the present invention underwent little changes upon both storages under high temperature conditions of 100° C. and under high temperature and humidity conditions of 60° C. and 90% RH, and were more resistant to light, compared with that of the comparative compound, and further the couplers of the present invention generated little stain due to the residual coupled in all discoloration tests. That is, the couplers of the present invention, which are characterized by an aryloxy group as an eliminable group, were ascertained to have no adverse influences with respect to heat, humidity, and light upon the dyes formed.

While the invention has been described in detail and with reference to specific embodiments thereof, it will be apparent to one skilled in the art that various changes and modifications can be made therein without departing from the spirit and scope thereof.

What is claimed is:

1. A silver halide color photographic material comprising a support having thereon at least one silver halide emulsion layer, wherein said material includes at least one 1H-pyrazolo(1,5-b)(1,2,4)triazole magenta coupler in which a substituted or unsubstituted aryloxy group is attached to the coupling active site.

2. A silver halide color photographic material as in claim 1, wherein the magenta coupler is represented by formula (I)

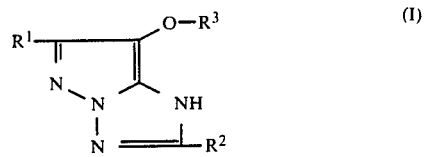

wherein
$R^1$ and $R^2$ each represents a hydrogen atom, a halogen atom, an aliphatic group, an aryl group, a heterocyclyl group, a cyano group, an alkoxy group, an aryloxy group, a heterocyclyoxy group, an acyloxy group, a carbamoyloxy group, a silyloxy group, a sulfonyloxy group, an acylamino group, an anilino group, a ureido group, an imido group, a sulfamoylamino group, a carbamoylamino group, an alkylthio group, an arylthio group, a heterocyclylthio group, an alkoxycarbonylamino group, an aryloxycarbonylamino group, a sulfonamido group, a carbamoyl group, an acyl group, a sulfamoyl group, a sulfonyl group, a sulfinyl group, an alkoxycarbonyl group, or an aryloxycarbonyl group;
$R^3$ represents an aryl group; or
$R^1$ or $R^2$ represents a divalent group including a simple bond through which the coupler forms a polymer, including a dimer; or $R^3$ represents an arylene group through which the coupler forms a polymer, including a dimer.

3. A silver halide color photographic material as in claim 2, wherein the aryl group represented by $R^3$ is an unsubstituted or substituted phenyl or naphthyl group.

4. A silver halide color photographic material as in claim 3, wherein the substituent of the substituted phenyl or naphthyl group is a halogen atom, an alkyl group, an aryl group, a heterocyclic group, a cyano group, an alkoxy group, an aryloxy group, a heterocyclyoxy group, an acyloxy group, a carbamoyloxy group, a silyloxy group, a sulfonyloxy group, an acylamino group, an anilino group, an amino group, a ureido group, an imido group, a sulfamoylamino group, an alkylthio group, an arylthio group, a heterocyclylthio group, an alkoxycarbonylamino group, an aryloxycarbonylamino group, a sulfonamido group, a carbamoyl group, an acyl group, a sulfamoyl group, a sulfonyl group, a sulfinyl group, an alkoxycarbonyl group, an aryloxycarbonyl group, a nitro group, a carboxyl group or a sulfo group.

5. A silver halide color photographic material as in claim 1, wherein the divalent group represented by $R^3$ when two coupler units of formula (I) form a bis compound through $R^3$ is a substituted or unsubstituted phenylene group, a naphthylene group, a biphenylene group, or a group represented by formula (II)

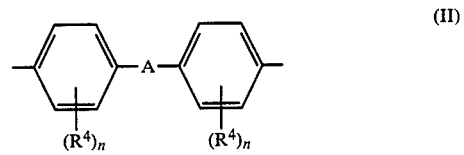

wherein A represents a divalent group, $R^4$ represents a substituent group and n is an integer of 0 to 4.

6. A silver halide color photographic material as in claim 1, wherein the divalent group represented by $R^1$ or $R^2$ when the coupler forms a bis compound therethrough is a substituted or unsubstituted alkylene or phenylene group, or a —NHCO—$R^5$—CONH— group wherein $R^5$ represents a substituted or unsubstituted alkylene or phenylene group.

7. A silver halide color photographic material as in claim 1, wherein the divalent group represented by $R^1$ or $R^2$ when the coupler of formula (I) is present in a vinyl monomer is a combined group formed by a connecting group selected from a class consisting of a substituted or unsubstituted alkylene group, a substituted or unsubstituted phenylene group, —NHCO—, —CONH—, —O—, —OCO— and an aralkylene group.

8. A silver halide color photographic material as in claim 1, wherein the coupler in the silver halide emulsion layer is present in a range of 0.003 to 0.5 mole per mole of silver halide.

* * * * *